United States Patent [19]

McCombs

[11] 4,325,878
[45] Apr. 20, 1982

[54] PROCESS FOR PREPARING 21-LOWER ALKOXYOXALYLPROGESTERONES

[75] Inventor: Charles A. McCombs, Kingsport, Tenn.

[73] Assignee: Eastman Kodak Company, Rochester, N.Y.

[21] Appl. No.: 239,799

[22] Filed: Mar. 2, 1981

[51] Int. Cl.$^3$ .............................................. C07J 7/00
[52] U.S. Cl. .................................................. 260/397.1
[58] Field of Search ..................................... 260/397.1

[56] References Cited

U.S. PATENT DOCUMENTS 2,698,852  1/1955  Beal et al. ...................... 260/397.1

FOREIGN PATENT DOCUMENTS 531922  10/1956  Canada ............................ 260/397.1
560480   7/1958  Canada ............................ 260/397.1
567782  12/1958  Canada ............................ 260/397.1

OTHER PUBLICATIONS

Chem. Abstracts, 58 (1963), Pars. 3494c, article by Azioni et al. (British Pat. 893,365).

*Primary Examiner*—Elbert L. Roberts
*Attorney, Agent, or Firm*—Clyde L. Tootle; Daniel B. Reece, III

[57] ABSTRACT

In accordance with the present invention, 21-lower alkoxyoxalylprogesterone is prepared in high yield by the lower alkoxyoxalylation of 3-methoxypregna-3,5-diene-20-one. The 3-methoxypregna-3,5-diene-20-one is prepared from progesterone by methods well known in the art. The 3-methoxypregna-3,5-diene-20-one is lower alkoxyoxalylated with an alkoxide base and the corresponding lower alkyloxalate in a suitable solvent. The alkoxide base consists of a lower alkoxide with an alkali metal counter ion. The lower alkyl group of both the alkoxide and oxalate should be the same and also are the same as the group to be added to the 21 position of the 20-keto steroid, the lower alkyl group contains 1 to 6 carbon atoms. The lower alkoxyoxalylation reaction can be carried at any temperature below the boiling point of the solvent and for a period of 2–20 hours depending on the temperature at which the reaction is carried out. For example, at elevated temperatures the rate of reaction is sufficiently fast to complete the lower alkoxyoxalylation in 2 to 4 hours whereas if the reaction is carried out at ambient temperatures complete reaction can require 14 to 20 hours. The reaction is preferably carried out under an inert atmosphere such as a nitrogen or argon atmosphere.

17 Claims, No Drawings

PROCESS FOR PREPARING 21-LOWER ALKOXYOXALYLPROGESTERONES

This invention relates to a novel process for preparing 21-lower alkoxyoxalylprogesterone by the lower alkoxyoxalylation of 3-methoxypregna-3,5-diene-20-one.

Methods for the 21-oxalylation of 20-keto steroids are known in the art for the preparation of various corticosteroid intermediates by the oxalylation of progesterone. One such process is the direct ethoxyoxalylation of progesterone using ethyl oxalate and sodium ethoxide reported in U.S. Pat. No. 2,727,905. However, it was subsequently shown by M. J. Weiss [*J. Amer. Chem. Soc.*, 82, 1709 (1960)] that progesterone, when subjected to these conditions, gave an indiscriminate mixture of 2-mono, 21-mono, and 2,21-bis- ethoxyoxalylprogesterones with only 60% overall conversion.

Another selective 21-ethoxyoxalylation of progesterone was reported by A. Ercoli and P. DeRuggiero [*Gazz. Chim. Ital.*, 84, 312 (1954)], and the regioselectivity was achieved by conversion of progesterone to its 3-ethylene ketal prior to ethoxyoxalylation. However, the overall yield of 21-ethoxyoxalylprogesterone was only 70% and the lengthy sequence of five processing steps was not suitable for large scale operations.

It would therefore be a significant advance in the state of the art to provide a simple high yield process for the preparation of 21-lower alkoxyoxalylprogesterone from progesterone in two steps.

In accordance with the present invention, 21-lower alkoxyoxalylprogesterone is prepared in high yield by the lower alkoxyoxalylation of 3-methoxypregna-3,5-diene-20-one. The 3-methoxypregna-3,5-diene-20-one is prepared from progesterone by methods well known in the art. One such method uses dimethoxypropane in dimethylformamide with an acid catalyst as reported by A. L. Nassbaum et al., *J. Org. Chem.*, 26, 3925 (1961). The 3-methoxypregna-3,5-diene-20-one is lower alkoxyoxalylated with an alkoxide base and the corresponding lower alkyloxalate in a suitable solvent. The alkoxide base consists of a lower alkoxide with an alkali metal counter ion. The lower alkyl group of both the alkoxide and oxalate should be the same and also are the same as the group to be added to the 21 position of the 20-keto steroid, the lower alkyl group contains 1 to 6 carbon atoms. The lower alkoxyoxalylation reaction can be carried at any temperature below the boiling point of the solvent and for a period of 2-20 hours depending on the temperature at which the reaction is carried out. For example, at elevated temperatures the rate of reaction is sufficiently fast to complete the lower alkoxyoxalylation in 2 to 4 hours whereas if the reaction is carried out at ambient temperatures complete reaction can require 14 to 20 hours. The reaction is preferably carried out under an inert atmosphere such as anitrogen or argon atmosphere.

Suitable solvents are polar, nonprotic solvents such as, for example, toluene, tetrahydrofuran and the like. The solvent is used in an amount, based on the weight of the steroid, of about 3 to 50 times by weight, preferably about 5 to 10 times. The use of the lower ratios 3 to 5 depends on the solubility of the reagents involved in the reaction.

The alkali metal lower alkoxide can be sodium methoxide, potassium methoxide, lithium methoxide, sodium ethoxide, potassium ethoxide, lithium ethoxide, sodium propoxide, potassium ethoxide, lithium ethoxide, sodium propoxide, potassium propoxide and the like. The amount of alkali metal lower alkoxide used is about 1 to 1.5 moles alkoxide per mole of steroid.

The lower alkyloxalate can be dimethyl oxalate, diethyl oxalate, dipropyl oxalate and the like. The amount of oxalate used is about 1 to 2 moles oxalate per mole of steroid.

The 21-lower alkoxyoxalyl-3-methoxypregna-3,5-diene-20-one, alkali metal salt can be separated and isolated, for example, by removing about half of the solvent and diluting the concentrated solution with ether. This causes the salt to precipitate and be isolated by filtration. The isolated salt can be converted to the free enol by protonation with acetic acid or other lower alkyl organic acids containing 2 to 10 carbon atoms. However, it is not necessary to isolate the alkali metal salt as the crude 21-lower alkoxyoxalylprogesterone can be obtained by removing solvent to about one quarter volume and partitioning between methylene chloride and 10% HCl solution. The acid treatment is necessary to protonate the metal salt and remove the methyl 3,5-dienol ether protecting group. The organic layer containing the crude 21-lower alkoxyoxalylprogesterone can then be dried over sodium sulfate and evaporated to provide the crude 21-lower alkoxyoxalylprogesterone. The crude 21-lower alkoxyoxalylprogesterone can be recrystallized from a lower alkanol such as, for example, methanol, ethanol, propanol and the like.

This invention can be further illustrated by the following examples, although it will be understood that these examples are included merely for purposes of illustration and are not intended to limit the scope of the invention unless otherwise specifically indicated.

EXAMPLE 1

21-Methoxyoxalyl-3-methoxypregna-3,5-diene-20-one, sodium salt

3-Methoxypregna-3,5-dien-20-one (1.0 g, 3.0 mmole) and dimethyl oxalate (0.72 g, 6.1 mmole) were dissolved in 10 ml tetrahydrofuran. To this was added powdered sodium methoxide (0.32 g, 6.0 mmole) and the mixture stirred 16 hours at ambient temperature under argon atmosphere. The solvent was removed to half volume and diluted with 25 ml ether. The precipitated product was stirred for 15 min. and filtered to afford 1.24 g (94%) of an amorphous yellow solid. An analytical sample was prepared by conversion of the sodium salt to its free enol by protonation with acetic acid. (Enol Anal. C: 72.43, H: 8.27; Found C: 72.05, H: 8.01).

EXAMPLE 2

21-Methoxyoxalylprogesterone

3-Methoxypregna-3,5-dien-20-one (20.0 g, 0.060 mole) and dimethyl oxalate (14.4 g, 0.120 mole) were dissolved in 100 ml tetrahydrofuran under argon atmosphere. To this was added powdered sodium methoxide (6.4 g, 0.120 mole) in one portion and the mixture stirred 16 hours at ambient temperature. The solvent was removed to one-quarter volume and partitioned between methylene chloride and a 10% HCl solution. The organic layer was separated, dried over sodium sulfate, and evaporated to afford the crude 21-methoxyoxalylprogesterone. After one recrystallization from methanol, 21.05 g (86%) of product was obtained as pale yellow crystals, mp 150°-151° C. (Anal. C: 71:97, H: 8.05; Found C: 72.05, H: 7.89).

EXAMPLE 3

21-Ethoxyoxalylprogesterone

3-Methoxypregna-3,5-dien-20-one (20.0 g, 0.050 mole) and diethyl oxalate (17.5 g, 0.120 mole) were dissolved in 100 ml tetrahydrofuran under argon atmosphere. To this was added powdered sodium ethoxide (8.3 g, 0.120 mole) in one portion and the mixture stirred 16 hours at ambient temperature. The reaction mixture was reduced to one-quarter volume and partitioned between methylene chloride and a 10% HCl solution. The organic layer was separated, dried over sodium sulfate, and evaporated to afford the crude 21-ethoxyoxalylprogesterone. After one recrystallization from methanol, 21.1 g (85%) of product was obtained as pale yellow crystals.

EXAMPLE 4

21-Methoxyoxalyl-3-methoxypregna-3,5-diene-20-one, potassium salt

3-Methoxypregna-3,5-dien-20-one (1.0 g, 3.0 mmole) and dimethyl oxalate (0.72 g, 6.1 mmole) were dissolved in 10 ml tetrahydrofuran. To this was added powdered potassium methoxide (0.42 g, 6.0 mmole) and the mixture stirred 16 hours at ambient temperature under argon atmosphere. The solvent was removed to half volume and diluted with 25 ml ether. The precipitated product was stirred for 15 min. and filtered to afford 1.30 g (96%) of an amorphous yellow solid.

The process of the present invention provides a method for the high yield synthesis of 21-lower alkoxyoxalylprogesterone from readily available progesterone. This method for preparing 21-lower alkoxyoxalylprogesterone by the selective lower alkoxyoxalylation followed by a mild hydrolysis is an important and valuable step in preparing corticosteroids.

I claim:

1. A process for preparing 21-lower alkoxyoxalyl-3-methoxypregna-3,5-diene-20-one, alkali metal salt from 3-methoxypregna-3,5-dien-20-one which comprises reacting 3-methoxypregna-3,5-dien-20-one with an alkali metal lower alkoxide base and a lower alkyloxalate in a suitable polar, nonprotic solvent.

2. A process according to claim 1 wherein said alkali metal lower alkoxide is sodium methoxide.

3. A process according to claim 2 wherein said lower alkyloxalate is dimethyloxalate.

4. A process according to claim 3 wherein said solvent is tetrahydrofuran.

5. A process for preparing 21-lower alkoxyoxalyl progesterone from 21-lower alkoxyoxalyl-3-methoxypregna-3,5-diene-20-one, alkali metal salt which comprises converting said alkali metal salt to the free enol by protonation with a lower alkyl organic acid containing 2 to 10 carbon atoms.

6. A process according to claim 5 wherein said lower alkyl organic acid is acetic acid.

7. A process for preparing 21-lower alkoxyoxalyl progesterone from 3-methoxypregna-3,5-dien-20-one which comprises reacting 3-methoxypregna-3,5-dien-20-one with an alkali metal lower alkoxide base and a lower alkyloxalate in a suitable polar, nonprotic solvent to form 21-lower alkoxyoxalyl-3-methoxypregna-3,5-dien-20-one, alkali metal salt and converting said alkali metal salt to the free enol by protonation with a lower alkyl organic acid containing 2 to 10 carbon atoms.

8. A process according to claim 7 wherein said lower alkyl organic acid is acetic acid.

9. A process according to claim 8 wherein said alkali metal lower alkoxide is sodium methoxide.

10. A process according to claim 9 wherein said lower alkyloxalate is dimethyloxalate.

11. A process according to claim 10 wherein said solvent is tetrahydrofuran.

12. 21-Methoxyoxalyl-3-methoxypregna-3,5-diene-20-one.

13. 21-Methoxyoxalyl-3-methoxypregna-3,5-diene-20-one, sodium salt.

14. 21-Methoxyoxalyl-3-methoxypregna-3,5-diene-20-one, potassium salt.

15. 21-Ethoxyoxalyl-3-methoxypregna-3,5-diene-20-one.

16. 21-Ethoxyoxalyl-3-methoxypregna-3,5-diene-20-one, sodium salt.

17. 21-Ethoxyoxalyl-3-methoxypregna-3,5-diene-20-one, potassium salt.

* * * * *